United States Patent [19]

Allison et al.

[11] Patent Number: 4,912,411
[45] Date of Patent: Mar. 27, 1990

[54] MAGNETO ACOUSTIC EMISSION APPARATUS FOR TESTING MATERIALS FOR EMBRITTLEMENT

[75] Inventors: Sidney G. Allison, Poquoson; Min Namkung, Tabb; William T. Yost, Newport News; John H. Cantrell, Tabb, all of Va.

[73] Assignee: The United States of America as represented by the Administrator of the National Aeronautics and Space Administration, Washington, D.C.

[21] Appl. No.: 210,486

[22] Filed: Jun. 23, 1988

[51] Int. Cl.⁴ .................. G01R 33/12; G01N 27/80
[52] U.S. Cl. ........................... 324/235; 73/801; 324/209; 324/226; 324/227; 324/239
[58] Field of Search .............. 324/209, 226, 227, 228, 324/235, 239; 73/577, 578, 587, 801

[56] References Cited

U.S. PATENT DOCUMENTS

| | | | |
|---|---|---|---|
| 4,408,160 | 10/1983 | King et al. | 324/209 |
| 4,481,470 | 11/1984 | Wallace | 324/228 |
| 4,599,563 | 7/1986 | Tiitto et al. | 324/232 |
| 4,647,856 | 3/1987 | Melgui et al. | 324/239 |
| 4,689,558 | 8/1987 | Ruuskanen et al. | 324/209 |
| 4,692,701 | 9/1987 | Dundas et al. | 324/240 |

FOREIGN PATENT DOCUMENTS

| | | | |
|---|---|---|---|
| 634188 | 11/1978 | U.S.S.R. | 324/209 |
| 849061 | 7/1981 | U.S.S.R. | 324/209 |
| 1062592 | 12/1983 | U.S.S.R. | 324/209 |

OTHER PUBLICATIONS

Ono et al; Magnetomechanical Acoustic Emission of Iron and Steels, Materials Evaluation/Jan. 1980, pp. 55–61.

Primary Examiner—Gerard R. Strecker
Attorney, Agent, or Firm—Harold W. Adams; John R. Manning; Charles E. B. Glenn

[57] ABSTRACT

A method and apparatus for testing steel components for temper embrittlement uses magneto-acoustic emission to nondestructively evaluate the component. Acoustic emission signals occur more frequently at higher levels in embrittled components. A pair of electromagnets are used to create magnetic induction in the test component. Magneto-acoustic emission signals may be generated by applying an AC current to the electromagnets. The acoustic emission signals are analyzed to provide a comparison between a component known to be unembrittled and a test component. Magnetic remanence is determined by applying a DC current to the electromagnets, then turning the magnets off and observing the residual magnetic induction.

9 Claims, 4 Drawing Sheets

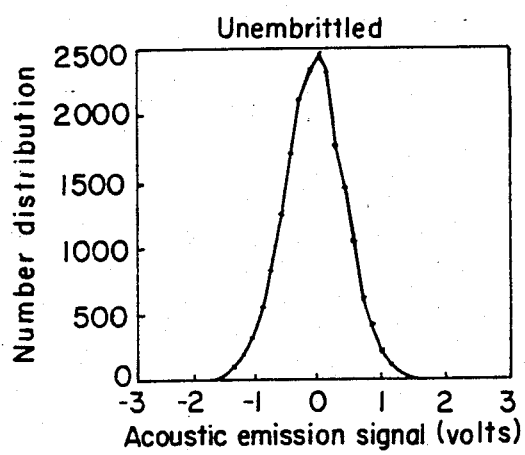
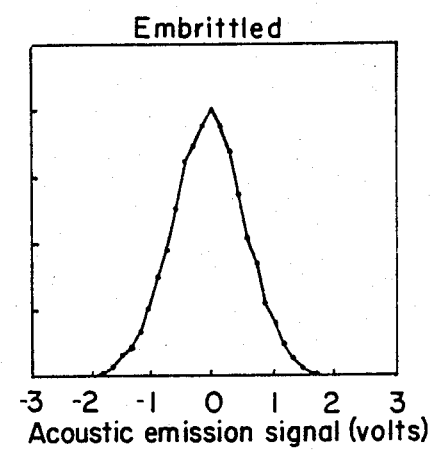
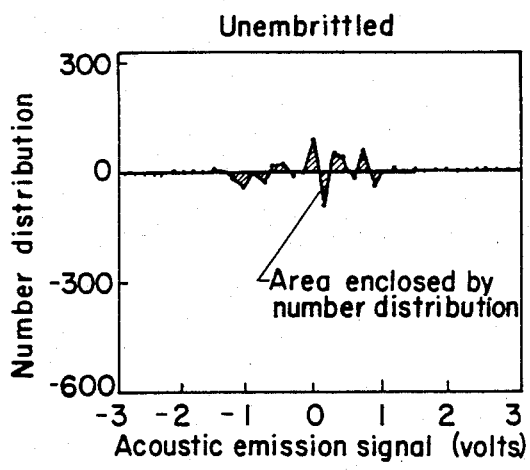
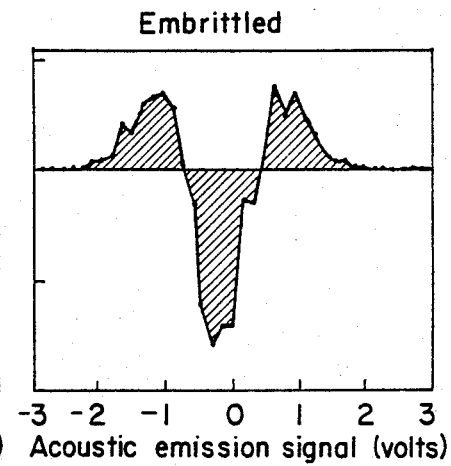
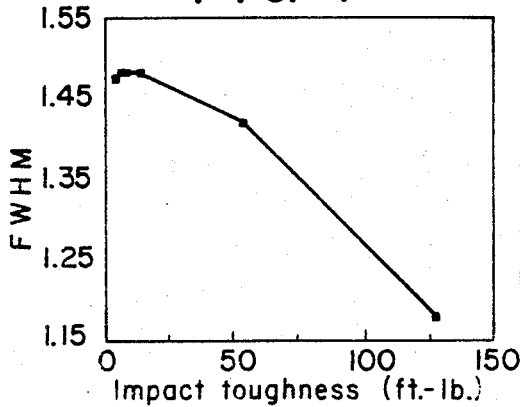
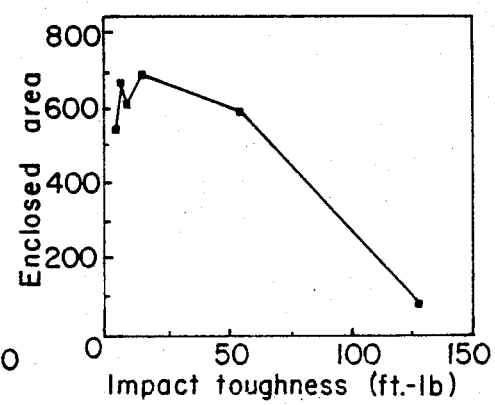

MAGNETO ACOUSTIC EMISSION APPARATUS FOR TESTING MATERIALS FOR EMBRITTLEMENT

ORIGIN OF THE INVENTION

The invention described herein was made by employees of the U.S. Government and may be manufactured and used by or for the Government for governmental purposes without the payment of any royalties thereon or therefor.

BACKGROUND OF THE INVENTION

1. Field of the Invention

The present invention relates generally to materials testing and, more specifically, to non-destructive testing for temper embrittlement in metals based on measurements of magneto-acoustic emission, magnetic remanence, and magneto-acoustic remanence.

2. Description of the Related Art

Temper embrittlement is the losso of impact toughness which occurs in susceptible alloy steel when heated within or slowly cooled through the temperature range of approximately 371° to 599° C. (700° to 1110° F.). The problem of temper embrittlement is caused by migration of impurity elements such as sulfur, phosphorus, tin, antimony, and arsenic to prior austenite grain boundaries. It has been known that although these embrittling elements are typically present in bulk weight percentage concentrations of 20 to 200 ppm, grain boundaries of embrittled steel can contain concentrations that are one or two orders of magnitude greater due to segregation during heat treatment.

Temper embrittlement does not occur in high purity steels. Unfortunately, the manufacture of high purity alloy steels is cost prohibitive. These high purity steels are used primarily when research grade materials are needed. Commercial grade steels, such as commercial grade HY80, which is a type of Ni-Cr-Mo-V alloy casting steel, contain various impurity elements which can cause temper embrittlement. Steels such as commercial grade HY80 are in extensive use today due to their high yield strength and high impact toughness. However, these properties can be degraded over time due to exposure to high temperatures. Temper embrittlement, which may be present in the material initially, or may develop over time, remains latent until a component made from the material fractures. Fracture of components used in the aerospace industry and elsewhere can result in loss of life or property, or both.

Presently, there are a number of testing techniques for determining the presence of temper embrittlement in metal components. Many commonly used testing procedures involve destructive mechanical testing, such as the well known Charpy V-Notch (CVN) test. In this test, a V-notch is cut into the specimen, and a sample is placed in an impacting device that records the amount of energy necessary to break the sample. The procedure is an expensive one which leaves a hole in the component. The hole must be filled with weld material after testing.

Non-destructive testing techniques are preferred for obvious reasons. One such non-destructive method is described in U.S. Pat. No. 4,408,160. There, it was recognized that a variable magnetic field results in the movement of domain walls which creates an acoustic wave known as the acoustic Barkhausen signal. The signal was found to vary in accordance with stress. A variable magnetic field was applied to a specimen so that, as the field varies, an acoustic vibratory wave was picked up by a transducer. The signal was amplified and filtered and then analyzed to determine pulse widths in a certain range which are characteristic of stress.

U.S. Pat. No. 4,692,701 describes a method of testing for temper embrittlement in steam turbine rotors. A coil was used to magnetize the specimen and produce a Barkhausen magnetic signal. The signals were compared to those of a non-embrittled rotor and an observable variance between the two determined specimen embrittlement.

U.S. Pat. No. 4,689,558 also describes a non-destructive testing technique which relies on the Barkhausen effect. The invention focuses on the determination of a fatigue limit of the specimen, which limit coincides with a maximum width root-mean-square (rms) value of the frequency of the Barkhausen signal.

SUMMARY OF THE INVENTION

An object of the invention is to provide a non-destructive method and apparatus for assessing temper embrittlement in steels.

Another object of the invention is to provide a method and apparatus for determining the presence o temper embrittlement in structural components without having to physically alter the components.

Another object of the invention is to provide a method and apparatus for testing temper embrittlement quickly and cost effectively.

In a preferred embodiment of the invention, a method for testing components for temper embrittlement includes the steps of applying an alternating magnetic field to a test component suspected of having temper embrittlement by supplying power to one or more electromagnets with an alternating current of a predetermined frequency and voltage, detecting acoustic emission signals from the test component with a transducer acoustically coupled to the test component, amplifying the detected acoustic emission signals with a first amplifier, filtering amplified acoustic emission signals to pass signals within a specified frequency range, measuring the filtered acoustic emission signals with an rms voltmeter to determine rms power as detected by the transducer, further amplifying the filtered acoustic emission signal with a second amplifier, the acoustic emission signal comprising a plurality of pulses having a plurality of voltages, selecting pulse voltages occurring during a predetermined time period relative to an envelope pattern of the acoustic emission signals, sampling a predetermined number of voltages at the acoustic envelope peaks with a sample/hold system, dividing the predetermined number of sampled pulse voltages into a predetermined number of equal voltage intervals, counting the number of voltages at each interval to form a pulse height distribution, forming a histogram based on the pulse height distribution, comparing the histogram of the test component to a similarly constructed histogram of a similar component known to be unembrittled, and determining the presence or absence of temper embrittlement based on the comparison, temper embrittlement being indicated by a wider histogram for the test component than for the control component, the wider histogram indicating a greater number of larger amplitude acoustic emission signals.

In another embodiment of the invention, an apparatus for measuring magneto-acoustic emission associated with a test component includes at least one electromagnet for generating a magnetic field in the test component. A line power regulator is connected to a source of alternating current and a variable transformer is connected to the line power regulator. A step-down isolation transformer is connected to the variable transformer, and a switch is connected to the step-down isolation transformer and to the electromagnet in order to selectively power the electromagnet. An acoustic emission transducer is acoustically coupled to the test component for detecting acoustic emission signals generated by magnetic field-induced domain wall motion. The output signal of the transducer is amplified. A sample/hold and timing generator selects signal voltages occurring during a predetermined time period relative to an envelope pattern of the acoustic emission signals and samples a predetermined number of voltages at the acoustic envelope peaks. A computer compares the selected voltages to those corresponding to a control component which is similarly tested, and the presence or absence of temper embrittlement is determined by a relative difference between the selected signals of an unembrittled component and the test component.

These objects, together with other objects and advantages which will be subsequently apparent reside in the details of construction and operation of the apparatus and method as more fully hereinafter described and claimed, reference being had to the accompanying drawings forming a part hereof, wherein like reference numerals refer to like parts throughout.

BRIEF DESCRIPTION OF THE DRAWINGS

FIG. 3a is a histogram of an unembrittled control component tested according to the system shown in FIG. 2;

FIG. 3b is a histogram of an embrittled test component tested according to the system shown in FIG. 2;

FIG. 4 is a graph of the full width at half maximum (FWHM), obtained from a fitted equation for a test component plotted against impact toughness;

FIG. 5a is a graph illustrating an area enclosed by a number distribution after subtracting two histograms for unembrittled steel;

FIG. 5b is a graph of the area enclosed by a number distribution after subtracting histograms for embrittled and unembrittled steels from each other;

FIG. 6 is a graph showing the results of subtraction in FIGS. 5a and 5b by plotting the enclosed areas against impact toughness;

DETAILED DESCRIPTION OF THE PREFERRED EMBODIMENTS

By way of example, a commercial grade HY80 casting steel was tested according to the method and apparatus of the present invention. The steel is quenched and tempered martensite made using the basic electric arc melting process. Water quenching from the austenite range forms martensite with some retained austenite and possibly some pearlite and bainite, depending on the cooling rate during quenching. The quenched material was then tempered at 649°–691° C. (1200°–1275° F.) to obtain the desired toughness while producing a yield strength of approximately 80 ksi. Temper embrittlement usually does not occur until after quenching and tempering, and is primarily brought about by post-fabrication heat treatment for stress relief. The heat treatment, unfortunately, usually requires heating within the embrittling temperature range.

Test samples were taken from an argon oxygen decarbonizing (AOD) processed material which was poured into a large test block. Metallurgical analysis revealed 0.0234 cm grain size and chemical composition weight percentages which includes 2.88 Ni, 1.4 Cr, 0.52 M, 0.009 V, 0.15 C, 0.20 P, 0.008 S, 0.006 Sn, 0.006 As and less than 0.002 Sb. The unembrittled quenched and tempered test block was cut into six slabs. One of the slabs was left unembrittled and the other five slabs were heat treated at 538° C. (1000° F.) for 1, 5, 24, 50 and 100 hours, respectively, to produce a different amount of embrittlement in each slab. Charpy V-Notch (CVN) impact tests were performed on each of the six slabs following heat treatment.

Figure 1:
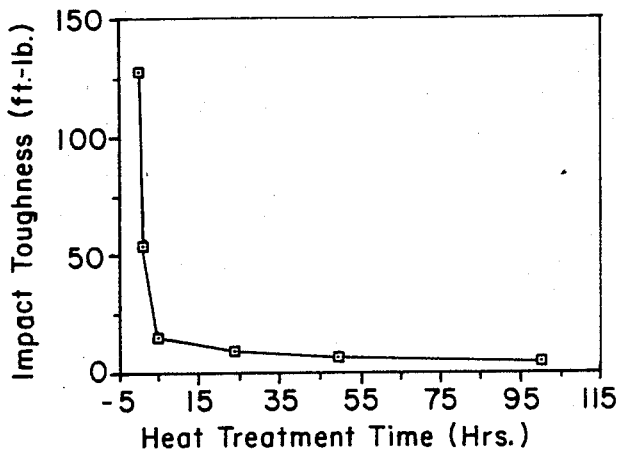
FIG. 1 is a graph showing temper embrittlement of tested HY80 steel, whereby impact toughness decreases with increasing heat treatment time.

Impact toughness was measured at −73, −18, and −1° C. (−100, 0, and +30° F.) test temperatures. FIG. 1 represents the results of the impact tests conducted at −1° C. FIG. 1 reveals a dramatic loss of impact toughness as a result of heat treatment. Examination of CVN fracture surfaces show the expected transgranular fracture for the unembrittled material and inter-granular fracture for the embrittled material. In contrast to these large changes in impact toughness, other mechanical properties, such as hardness, yield strength, and ultimate strength, change very little with embrittling heat treatment.

Figure 2:
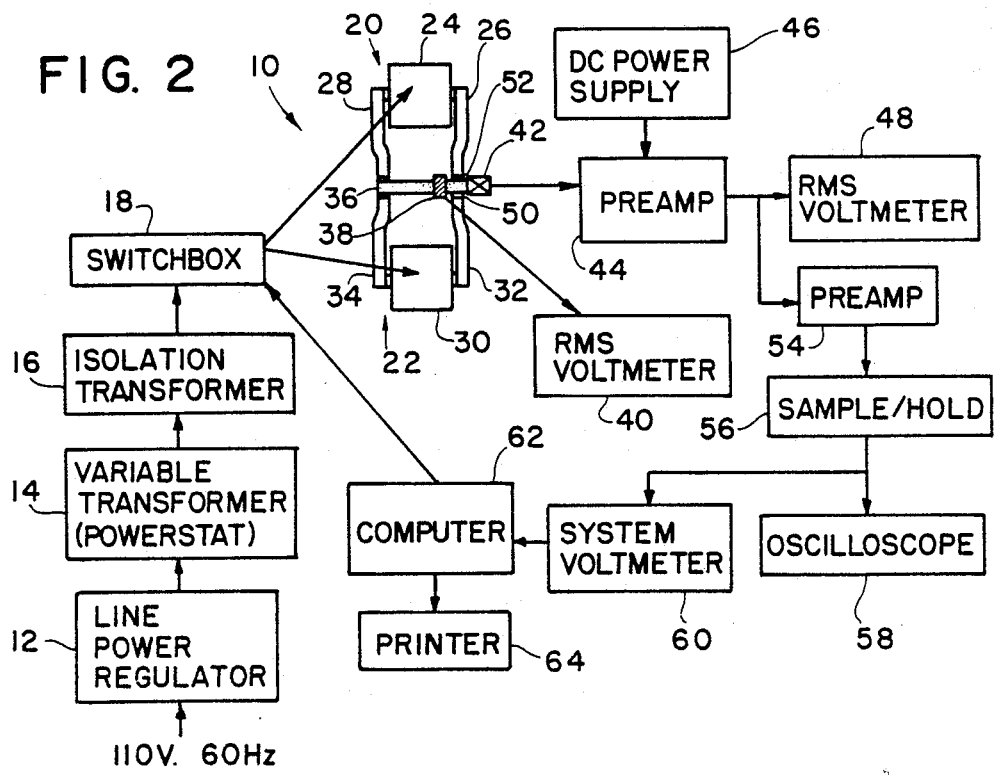
FIG. 2 is a schematic diagram of a preferred embodiment of the present invention.

A system according to the present invention and used for testing the test samples is illustrated in FIG. 2. FIG. 2 illustrates a magneto-acoustic emission (MAE) measurement system 10 having a 60 Hz, 110 volt power source stabilized by a line power regulator 12. The power source is made adjustable by a variable transformer 14 which supplies variable power through a step-down isolation transformer 16 to a switch box 18.

The switch box 18 supplies power to a pair of water-cooled electromagnets 20 and 22. The step-down isolation transformer 16 decreases the output of the variable transformer 14 and provides isolation from the AC electrical service which supplies the power source. The switch box 18 provides power to the electromagnets 20 and 22. Electromagnet 20 has a coil 24 and pole pieces 26 and 28. Similarly, electromagnet 22 has a coil 30 and pole pieces 32 and 34. The electromagnets 20 and 22 externally apply an alternating magnetic field to a test component 36. By placing one electromagnet on each side of the test component 36, a symmetric magnetic field is produced throughout the test component.

A pick up coil 38 detects the rate change of magnetic induction and outputs a voltage signal, the phase of which may be used (not shown) to trigger the sample and hold circuit and the oscilloscope. This triggering of the oscillioscope 58 permits the automation of the testing apparatus. The coil 38 is also used to duplicate peak magnetic induction intensity in the test materials from one sample to the next, and provides means for determining the level of magnetic induction in test sample. An RMS voltmeter 40 is used to measure coil output voltage. An acoustic emission (AE) transducer 42 is acoustically coupled to the test component 36. The AE transducer 42 is preferably shielded against stray magnetic field interference by layers of thin Mu-metal sheets or other shielding material, if necessary. This prevents unwanted signals from being generated by the transducer thereby interfering with acoustic signals produced by the test component. Certain types of transducers do not produce interfering signals and would not need shielding. The AE signals from the AE transducer 42 are amplified 60 dB by preamp 44 and filtered to pass frequencies from 125 kHz to 1 MHz. Preamp 44 is powered by a DC power supply 46. AE signals are measured by an rms voltmeter 48, such as the model 3400A rms voltmeter produced by Hewlett Packard. The rms voltmeter 48 makes it possible to determine the rms power detected by the AE transducer 42. This information is used in setting up each measurement to assure that the AE transducer 42 is well bonded to the test component 36. Acoustic isolation, e.g., foam rubber pads 50 and 52 isolate the sample 36 from the magnet cores/poles 20 and 22, thereby eliminating extraneous noise associated with the electromagnets. The test component 36 as well as the electromagnets 20 and 22 are grounded by conductive straps (not shown) to help further eliminate interference signals that distort the MAE measurements.

The AE signal is further amplified 40 dB in preamp 54 and is passed to a sample/hold and timing generator system 56 which establishes a time window that is positioned to select voltages at a desired phase relative to the pick-up coil output. An oscilloscope 58 powered by and synchronized to be triggered with the 110V, 60 Hz supply voltage as well known is used to observe the AE signal forms and the simple/hold marker. The timing for the sample/hold is set to select voltages at the peak of the AE signal envelope. These selected voltage signals pass through system voltmeter 60 to a computer 62 used to record the results. Pulse height analysis of the voltage signals was performed. In the test conducted on the slabs of HY80 steel, 41 equal voltage intervals were selected and the resulting distributions were plotted. FIGS. 3a and 3b are histograms of 20,000 AE pulse heights divided among the voltage intervals, FIG. 3a represents an unembrittled sample and FIG. 3b represents an embrittled specimen (1 hour heat treatment). Data outside the center region of the pulse height distribution is fitted by a gaussian distribution function. The center region of the pulse height distribution is not used in the gaussian fit because it is rich in extraneous noise. The full width at half maximum (FWHM) is obtained from the fitted equation for each sample and is plotted against impact toughness as shown in FIG. 4. This illustrates the differences in pulse height distribution between embrittled and unembrittled steel. Basically, histograms for embrittled steel are wider than those for unembrittled steel. These observations regarding pulse height distribution indicate that the embrittled steels produce a greater number of larger AE events than do unembrittled steels.

With the knowledge that embrittled steels produce more of the larger AE events than unembrittled steels, a model is established based on the concept that grain boundaries of embrittled steel are larger obstacles to magnetic domain wall motion than are grain boundaries of unembrittled steel. The phenomena of embrittled steel producing more of the larger AE events than does unembrittled steel is best explained in terms of the magnetoelastic-type interaction between domain walls (mostly 90° domain walls) and grain boundaries.

The action of magnetic domain walls jumping across larger obstacles produces larger AE events. The enhanced concentration of tramp materials at grain boundaries of embrittled steel causes these grain boundaries to become larger obstacles to domain wall motion.

For additional differentiation between embrittled and unembrittled samples, histograms from the MAE tests, previously illustrated in FIGS. 3a and 3b, are subtracted from each other and the area enclosed by the number distribution is calculated. Histograms from two separate measurements obtained for the unembrittled steel with the transducer re-bonded for each measurement are subtracted from each other. The results are illustrated in FIG. 5a. The unembrittled sample histogram is then subtracted from histograms for each of the embrittled steels and the enclosed areas associated with these subtractions are calculated. The results of the subtraction for a test component heat treated for one hour is illustrated in FIG. 5b. Finally, in FIG. 6, these enclosed areas are plotted against impact toughness. FIG. 6 reveals that by duplicating the magnetic power level in samples of identical geometry taken from the same quenched and tempered casting, and using the same transducer consistently well bonded, differences in MAE corresponding to temper embrittlement are observed that allow distinction between unembrittled and embrittled steel. The illustrated results, of course, are from testing of HY80 steel. Similar results are expected for other similar steels.

The measured MAE signals which results from the alternating magnetic field applied by electromagnets 20 and 22 are basically separated into size categories to form the histograms illustrated in FIGS. 3a and 3b. The histogram for unembrittled steel, FIG. 3a, is subtracted from that of an embrittled steel, FIG. 3b, thereby yielding an area enclosed by the number distribution. FIG. 5a shows the subtraction of two histograms for unembrittled steel, while FIG. 5b shows the subtraction of histograms for unembrittled steel from an embrittled steel. The enclosed area is illustrated in FIG. 6 as varying with the amount of embrittlement, thereby allowing a distinction to be made between embrittled and unembrittled steel.

Figure 7:
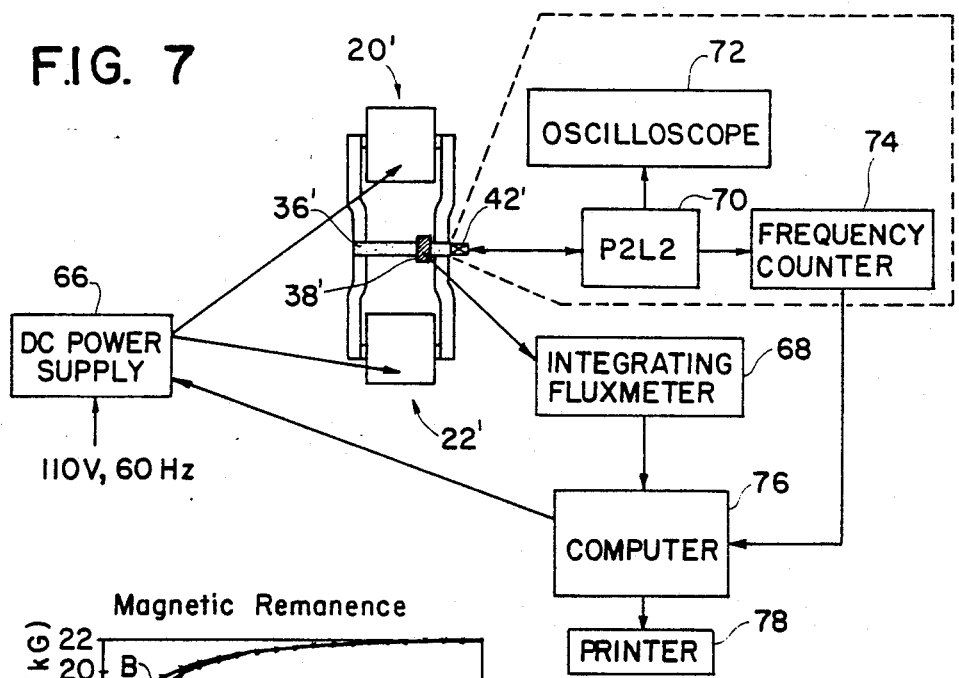
FIG. 7 is a schematic diagram of a second preferred embodiment of the present invention.
Figure 8:
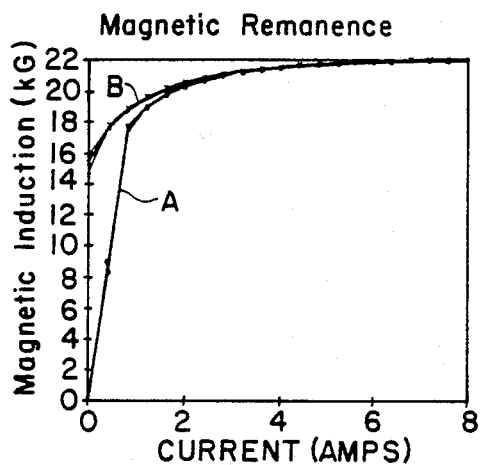
FIG. 8 is a graph illustrating the results of magnetic reminence measurements on test components.
Figure 9:
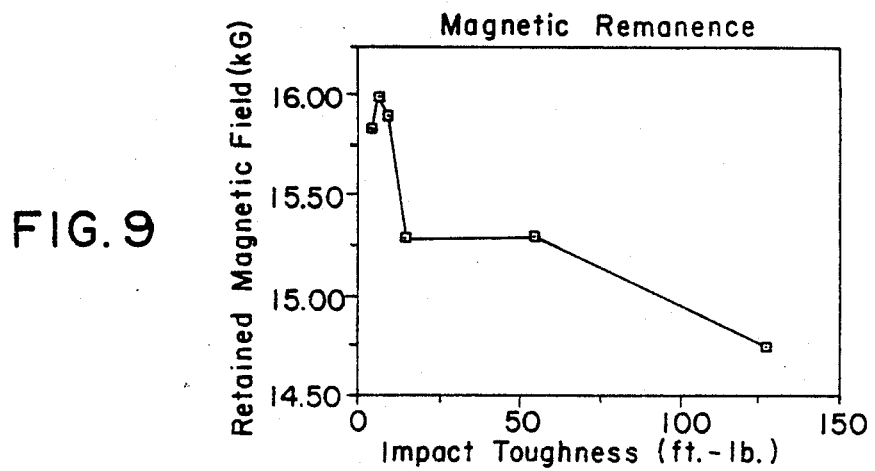
FIG. 9 is a graph comparatively showing magnetic remanence of embrittled and unembrittled steel.

Embrittlement may also be tested according to the system illustrated in FIG. 7, which shows a magnetoacoustic remanence measurement system and a magnetic remanence measurement system. In either system, measurements may be taken to test for temper embrittlement using the same electromagnets 20' and 22'. These are identical to electromagnets 20 and 22 previously described with reference to FIG. 2, except that the AC power source is replaced by a DC power supply 66. To measure remanence, the electromagnets 20' and 22' magnetize the test component 36', while a calibrated pick up coil 38' outputs a signal to an integrating flux meter 68. The outputted signals, which are read by the integrating flux meter 68, indicate magnetic induction in the test sample. Each test sample is initially demagnetized using a degaussing procedure. After demagnetization, incrementally increasing electromagnet current is applied as illustrated in FIG. 8, part A, until the test sample is magnetically saturated. Electromagnet power is then incrementally decreased to zero as illustrated in FIG. 8, part B, and the amount of magnetic field retained after turning the electromagnets off is measured. In the test conducted on the HY80 steel slabs, the results of the magnetic remanence measurements are illustrated in FIG. 9, where remanence (or retentivity) measured in kilogauss (KG) for each of the six samples is plotted against known impact toughness.

These results show that when the externally applied magnetic field is removed, the embrittled samples retain more magnetic field than the unembrittled sample. These remanence test results point to the same conclusion as the MAE results which were previously described, i.e., grain boundaries of embrittled steel are larger obstacles to magnetic domain wall motion than are grain boundaries unembrittled steel. By magnetizing the test sample to a point of magnetic saturation, the magnetic domain walls are forced to cross over grain boundaries. Upon removing the applied magnetic field, magnetic domain walls attempt to move back across grain boundaries. The magnetic domain walls hang up more on grain boundaries of embrittled steels than on grain boundaries of unembrittled steel. When the magnetic field is applied step-wise to the test component 36', the embrittled steels retain more magnetic field than the unembrittled steels. This is illustrated in FIG. 8, which shows data for the unembrittled steel and two of the embrittled steels. After applying enough current to the electromagnets to magnetically saturate the test material, the magnets are turned off and the amount of residual magnetic induction is the final data point for each magnetization curve. Thus, FIG. 9 shows that higher retained magnetic fields result for the embrittled steels (having low impact toughness) compared to the unembrittled steel.

Figure 10:
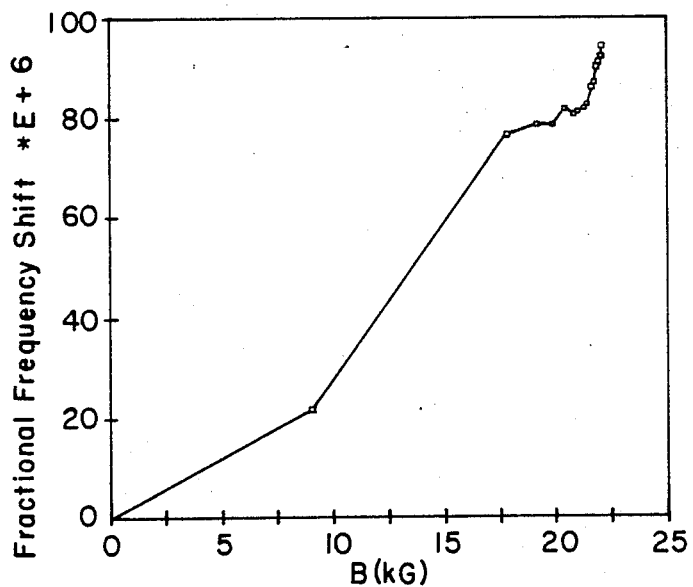
FIG. 10 is a graph showing field-induced velocity change of sound waves for a test component.
Figure 11:
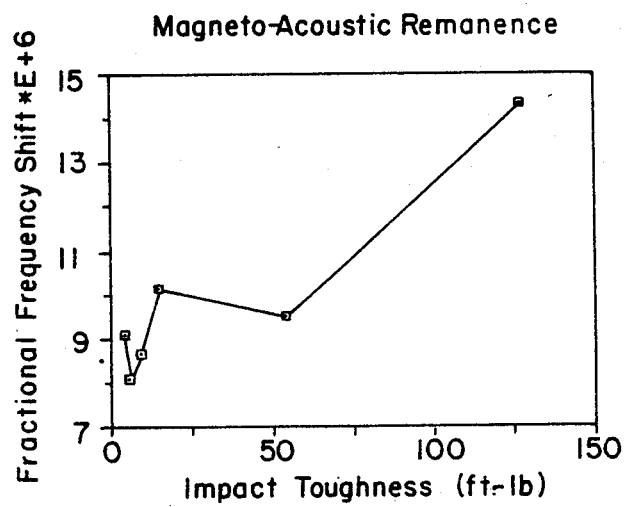
FIG. 11 is a graph illustrating how the amount of field-induced velocity change varies with the amount of embrittlement.

Another embodiment of the invention involves measuring magneto-acoustic remanence with an ultrasonic transducer 42' which is coupled to an ultrasonic pulsed phase locked loop measurement system (P2L2) 70 which is connected to an oscilloscope 72 and a frequency counter 74. The frequency counter 74 is connected to a computer 76 which has an associated printer 78. Computer 76 and printer 78 can be used to formulate results in a manner similar to that in the FIG. 2 embodiment. FIG. 10 shows a typical magneto-acoustic remanence measurement in which the applied magnetic field causes a change in the natural velocity of sound waves. FIG. 11 shows that by plotting fractional frequency shift on the Y-axis and impact toughness on the X-axis, the amount f field-induced velocity change is seen to vary with the amount of embrittlement.

While the present invention has been described in the context of temper embrittlement, other types of embrittlement based on the grain boundary phenomenon could be tested, such as hydrogen embrittlement.

The many features and advantages of the present invention are apparent from the detailed specification, and thus, it is intended by the appended claims to cover all such features and advantages of the method and apparatus for testing materials by magneto-acoustic emission, magneto-acoustic remanence, and magnetic remanence which fall within the true spirit and scope of the invention. Further, since numerous modifications and changes will readily occur to those skilled in the art based upon the disclosure herein, it is not desired to limit the invention to the exact construction and operation illustrated and described. Accordingly, all suitable modifications and equivalents may be resorted to falling within the scope and the spirit of the invention.

What is claimed is:

1. An apparatus for testing materials for embrittlement comprising:
    electromagnet means;
    a source of alternating current for energizing said electromagnet means to generate magnetic induction in said materials;
    an acoustic emission transducer means acoustically coupled to the material under test for detecting acoustic emission signals generated in an envelope pattern by magnetic domain wall motion produced in said material by said magnetic induction therein and producing corresponding signal voltage pulses;
    sample/hold and timing generator means coupled to said acoustic emission transducer means for selecting those signal voltage pulses occurring during a predetermined time period relative to the envelope pattern of said acoustic emission signals and for sampling a predetermined number of voltage pulses at the acoustic envelope peaks; and
    means responsive to said sample/hold and timing generator means to analyzing and relating the heights of said predetermined number of signal voltage pulses to the embrittlement of said material.

2. An apparatus as recited in claim 1 said source of alternating current further comprising a line power regulator, a variable transformer connected to the line power regulator, a step-down isolation transformer connected to the variable transformer, and a switch connected to the step-down isolation transformer and to the electromagnetic means for selectively powering the electromagnetic means.

3. An apparatus as recited in claim 2, further comprising means for comparing the heights of said predetermined number of signal voltage pulses in a test material to signal voltage pulses in an unembrittled component of said material, the presence or absence of embrittlement being determined by a relative difference between the respective pulse heights of said signal voltages pulses, a greater number of signal voltage pulses or larger height being indicative of embrittlement.

4. An apparatus as recited in claim 3, further wherein said means for analyzing and relating includes means for separating signal voltage pulses into size categories to form a histogram for both the unembrittled component and the test component, the histogram for the unembrittled component being subtracted from that of the test component thereby yielding a difference in area which is indicative of embrittlement.

5. An apparatus as recited in claim 3, wherein the electromagnet means comprises two water cooled electromagnets.

6. An apparatus as recited in claim 2, wherein the step-down isolation transformer decreases the output of the variable transformer to a level compatible with measurement needs.

7. An apparatus as recited in claim 1, further comprising a magnetic induction pick up coil disposed adjacent the test component for detecting changes in magnetic induction.

8. An apparatus as recited in claim 7, further comprising an rms volt meter coupled to the magnetic induction pick up coil for indicating the level of magnetic induction.

9. An apparatus as recited in claim 5, further comprising foam rubber pads disposed between the two electromagnets and the test component for removing acoustic interference associated with the two electromagnets.

* * * * *